United States Patent [19]
Kakimoto

[11] Patent Number: 5,252,067
[45] Date of Patent: Oct. 12, 1993

[54] HANDPIECE FOR DENTAL MEDICAL TREATMENT

[75] Inventor: Yasuo Kakimoto, Aichi, Japan

[73] Assignee: Ushio Co., Ltd., Aichi, Japan

[21] Appl. No.: 829,249

[22] Filed: Feb. 3, 1992

[30] Foreign Application Priority Data

Dec. 3, 1991 [JP] Japan .................. 3-319072
Dec. 16, 1991 [JP] Japan .................. 3-332091

[51] Int. Cl.⁵ .................................................. A61C 1/14
[52] U.S. Cl. .................................... 433/129; 433/84;
433/126; 433/132
[58] Field of Search ............... 433/82, 84, 126, 129,
433/132

[56] References Cited

U.S. PATENT DOCUMENTS

| | | | |
|---|---|---|---|
| 1,701,172 | 2/1929 | Brown | 433/126 |
| 3,074,167 | 1/1963 | Turchi et al. | 433/129 |
| 3,252,719 | 5/1966 | Borden | 433/132 |
| 3,955,284 | 5/1976 | Balson | 433/132 |
| 4,211,009 | 7/1980 | Leonard | 433/126 |
| 4,219,330 | 8/1980 | Jaremus | 433/126 |
| 4,348,180 | 9/1982 | Schuss | 433/126 |
| 4,661,060 | 4/1987 | Strohmaier | 433/82 |
| 5,057,015 | 10/1991 | Fleer | 433/126 |
| 5,074,750 | 12/1991 | Kahimoto | 433/114 |

*Primary Examiner*—John J. Wilson
*Attorney, Agent, or Firm*—Sandler Greenblum & Bernstein

[57] ABSTRACT

The present invention provides a handpiece for dental medical treatment in which a head portion encasing therein an air turbine is detachably mounted on a handpiece body whereby the handpiece body capable of being subjected to high temperature sterilization by boiling is repeatedly used whereas the head portion is discarded after use to maintain the aseptic state of the whole handpiece and positively prevent secondary infection such as AIDS, hepatitis, etc. in an actual medical site. Furthermore, the construction of the air turbine and molding of various parts are simplified so that the head portion can be provided at extremely low cost to effectively prevent infection of AIDS, hepatitis, etc. as mentioned above.

3 Claims, 4 Drawing Sheets

HANDPIECE FOR DENTAL MEDICAL TREATMENT

BACKGROUND OF THE INVENTION

1. Field of the Invention

The present invention relates to a handpiece for dental medical treatment used for removing and cutting treatments of the affected tooth part.

2. Description of the Prior Art

In a conventional handpiece of this kind, an air turbine is encased in a head portion at the extreme end of a handpiece body and a spray port for a cooling water is provided. A cutting tool is inserted into a tubular rotary shaft of the air turbine. The air turbine is driven by compressed air which flows through air supply and discharge flowpassages within the handpiece body whereby the cutting tool rotates at high speed to remove and cut the affected tooth part.

Incidentally, the greatest problem in the recent dental medical field is to prevent the secondary infection of AIDS (Acquired Immune Deficiency Syndrome), hepatitis, etc. The conventional handpiece constructed as described above can be mentioned as one of those which most likely comprises an infectious medium in the actual medical site.

That is, in order to prevent infection of the virus infectious symptoms, high temperature sterilization by boiling is most effective. However, in the conventional handpiece, the air turbine encased in the head portion thereof is not formed so as to withstand the high temperature sterilization by boiling. It is contemplated in order to overcome this problem that the high temperature durability of the air turbine is improved or a sterilization method by a sterilization gas is used. In the case of employing these means, however, there possibly brings forth an increase of manufacturing cost of a handpiece or expenses for sterilization, and accordingly, high cost of medical expenses and a substantial increase of a burden by patients.

The present invention has been accomplished in view of the circumstances noted above with respect to prior art. It is a primary object of the present invention to employ a sterilization method by boiling which is most effective and inexpensive for prevention of infection and to maintain an aseptic condition of the whole handpiece without requiring of improving high temperature durability of an air turbine. A second object of the invention is to realize the aforesaid primary object at extremely low cost.

SUMMARY OF THE INVENTION

For achieving the aforesaid first object, a handpiece for dental medical treatment according to the present invention is characterized in that a head portion is formed separately from a handpiece body, a tubular portion slipped over an extreme end of the handpiece body is provided at a rear end thereof, air supply and discharge ports through which air supply and discharge flowpassages and a turbine chamber for an air turbine are communicated and a cooling water port and a spray air port through which a cooling water flowpassage and an air flowpassage are communicated with a spray port are bored at an inner end of said tubular portion, and an anti-slip projection is provided on one of an inner periphery of the tubular portion of said head portion and an outer periphery at the extreme end of the handpiece while a recess with which said projection is disengageably and elastically engaged is provided on the other.

For achieving the aforesaid second object, it is effective that said head portion is formed with a closed-end tubular receiving chamber an upper surface of which is opened, upper and lower bearings, a rotary shaft upper and lower ends of which are supported by said bearings, a turbine provided integral with the outer periphery of said rotary shaft, and an elastic member for urging said bearings and said turbine toward the upper surface of the receiving chamber are charged into said receiving chamber, and a lid member is fitted to an opening of the upper surface of the receiving chamber to form an air turbine.

Moreover, walls in sliding contact with upper and lower edges of the turbine are provided on upper and lower inner rings slipped over the rotary shaft to form a turbine chamber between both the walls, lid portions opposed to said walls are provided on upper and lower outer rings surrounding the respective inner rings, and a plurality of steel balls are received between said inner rings and said outer rings to form upper and lower bearings.

Furthermore, a tapped hole is provided internally of an upper end of a collet inserted into the rotary shaft, and a stop screw engaged with said tapped hole is engaged at the end of the rotary shaft so that said collet is threadedly moved forward and backward by turning said stop screw to tightly hold a cutting tool inserted into a slotted mounting hole of the lower end of the collet.

According to the aforementioned structure, when the extreme end of the handpiece body is forced into the tubular portion of the head portion, the anti-slip projection and the recess are elastically engaged with each other. Thereby, the head portion is attached to the extreme end of the handpiece body in a one-touch manner. Under this condition, the air supply flowpassage and discharge flowpassage in the handpiece body are communicated with the turbine chamber for the air turbine, and the cooling water flowpassage and air flowpassage are communicated with the spray port for cooling water to render possible the high speed rotation of the cutting tool caused by the drive of the air turbine, spraying of cooling water and dental treatment thereby.

After completion of the treatment, if the handpiece body and the head portion are pulled in directions opposed to each other, the engagement between the anti-slip projection and the recess is released so that the head portion can be removed from the handpiece body in a one touch manner. The removed head portion (the used head portion) is discarded. After the handpiece body has been subjected to high temperature sterilization by boiling, an unsed new head portion is attached to the extreme end of the handpiece body as mentioned above to carry out treatment for a next patient.

With the provision of structure defined, only the spray port for cooling water formed in the head portion need be subjected to secondary working by a drill or the like but parts except those mentioned above, namely, all parts constituting a casing for a head portion, an air turbine, a support mechanism for a cutting tool and the like can be provided by molding which requires no secondary working. Further, an internal construction of a head portion comprised of these parts is of a simple configuration, making it possible to provide a head portion at an extremely low cost.

DETAILED DESCRIPTION OF THE PREFERRED EMBODIMENTS

Figure 1:
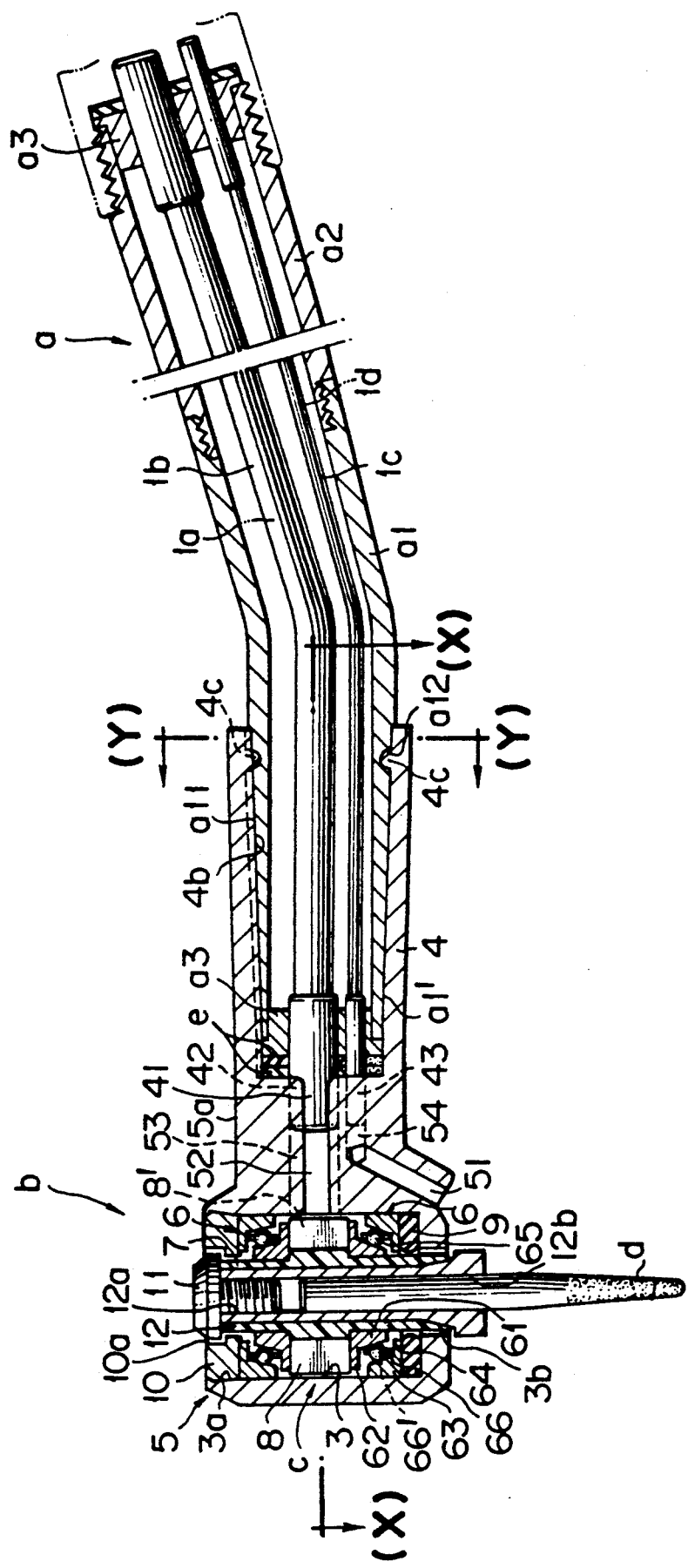
FIG. 1 is a longitudinal sectional view showing one embodiment of a handpiece for dental medical treatment.
Figure 2:
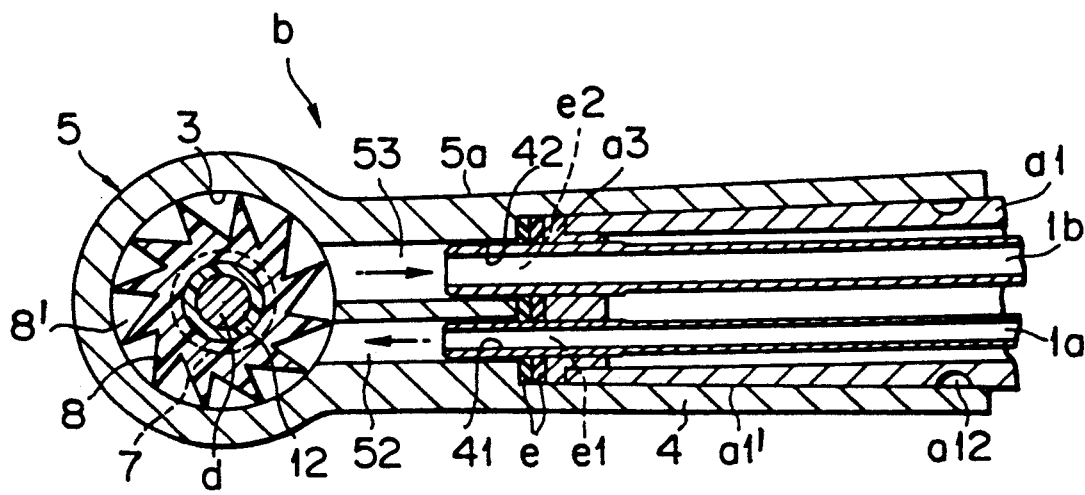
FIG. 2 is an enlarged sectional view taken along line X—X.

One embodiment of a handpiece for dental medical treatment in which a head portion b is detachably attached to an extreme end of a handpiece body a through elastic engaging means comprised of an anti-slip projection and a recess will be described hereinbelow with reference to FIGS. 1 to 5. In the present embodiment, an anti-slip projection 4c is provided on the side of the head portion b, and a recess a12 is provided on the side of the hand-piece body a.

In order that the handpiece body a can be used for long periods, it is designed so that a tubular front case a1 and a rear case a2 formed of metal having a desired durability are threadely fitted and connected to form an interiorly hollow pencil type configuration, lids a3 are fixedly mounted on openings at opposite ends thereof, and pressure-resistant and heat-resistant pipes for compressed air supply flowpassage 1a and discharge flow passage 1b, cooling water flowpassage 1c and an air flowpassage 1d for spraying of cooling water are inserted therein to form the respective flowpassages 1a to 1d. The fore-end and rear end of the pipes for forming the respective flowpassages 1a to 1d are projected from the lids a3. The fore-end and rear end are communicated with the head portion b and a supply source for compressed air or cooling water, respectively.

The fore-end of the handpiece body a, that is, the outer periphery of the end a1' of the front case a1 is formed to be a substantially drum-shape that can be inserted into a tubular portion 4 later described (see FIG. 3), and the handpiece body is formed in its outer peripheral surface with a key way a11 into which a key 4b is fitted, and an annular recess a12 with which each projection 4c is disengageably elastically engaged.

The head portion b is interiorly provided at the fore-end with a receiving chamber 3 and at the rear end with a casing 5 having a tubular portion 4 slipped over the fore-end of the handpiece body a, said casing 5 being integrally formed of synthetic resin or metal, said receiving chamber 3 receiving therein an air turbine c.

The tubular portion 4 is formed in its inner end wall with an air supply port 41, an air discharge port 42, a cooling water port 43, and a spray air port 44 into which are inserted extreme ends of pipes for forming the aforementioned flowpassages 1a to 1d. In an intermediate portion 5a for connecting the tubular portion 4 with the receiving chamber 3 are formed passages 52 and 53 for communicating a cooling water spray port 51, said air supply port 41 and said air discharge port 42 with a turbine chamber 8' later described, and passages 54 and 55 for communicating said cooling water port 43 and said spray air port 44 with the spray port 51.

Figure 3:
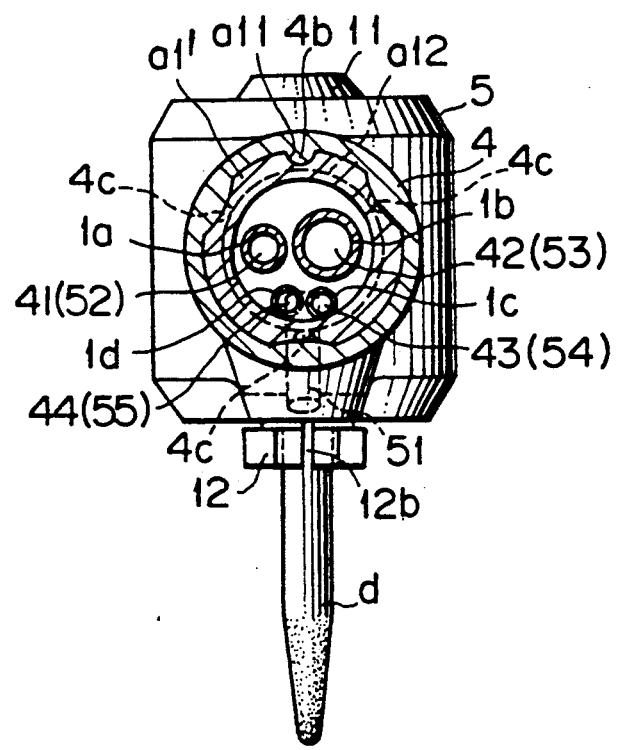
FIG. 3 is an enlarged sectional view taken along line X—X of FIG. 1.
Figure 4:
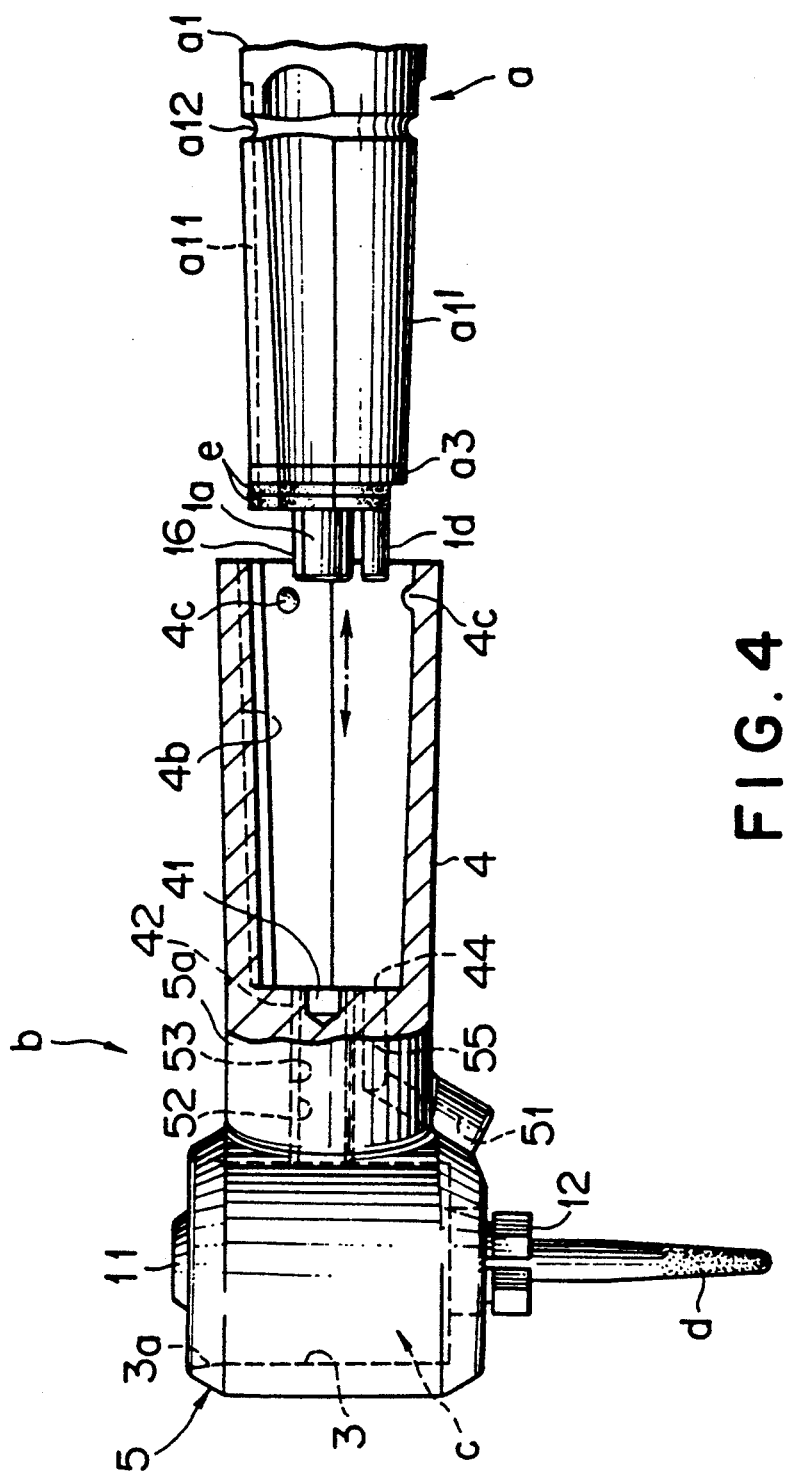
FIG. 4 is a side view showing the state in which a head portion is removed, partly being cutaway.
Figure 5:
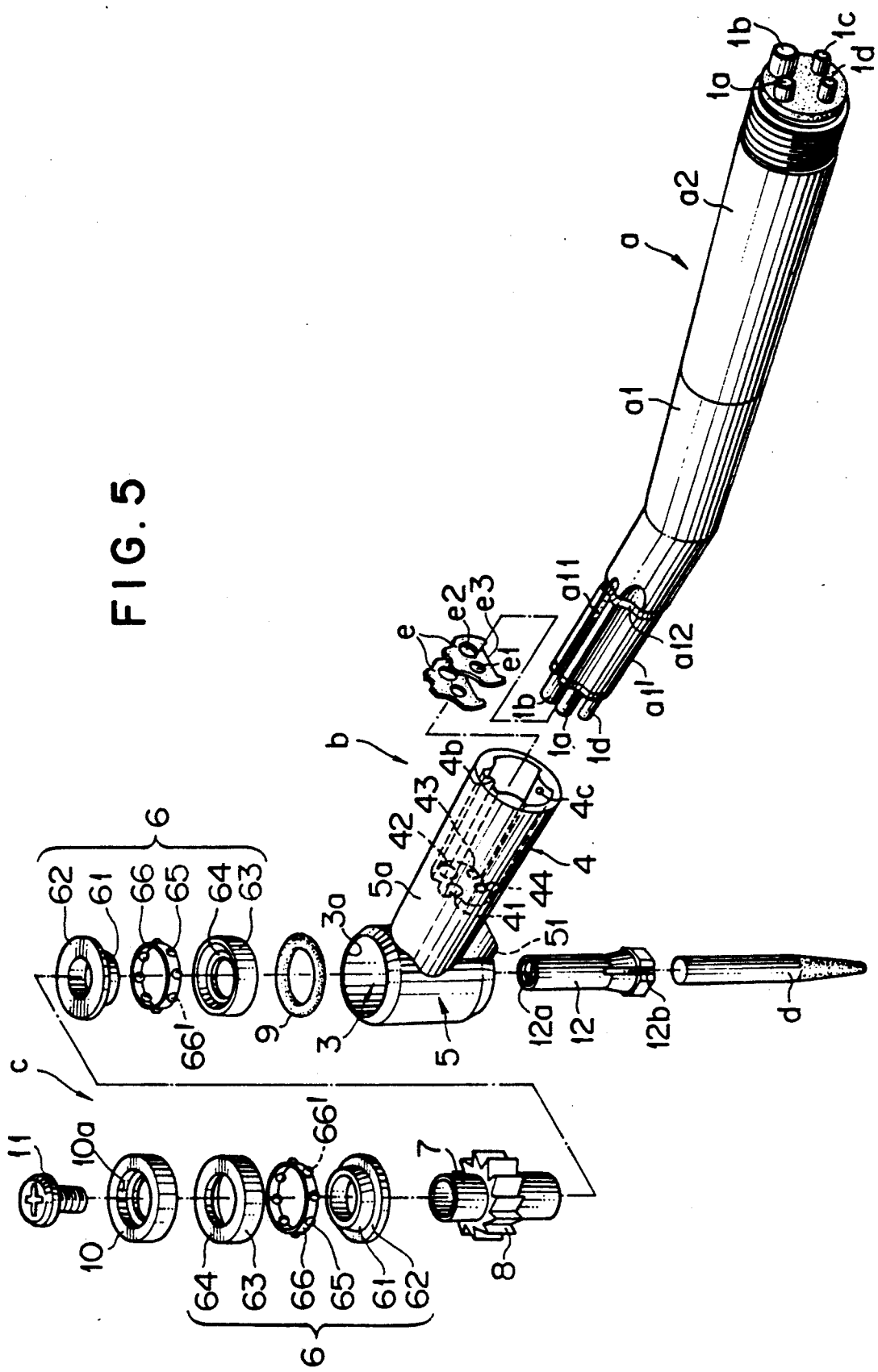
FIG. 5 is a perspective view of a head portion in its exploded form.

The tubular portion 4 is formed in its inner periphery to be a substantially drum-shape as shown in FIG. 3, and is formed in its inner peripheral surface with a locating key 4b extending in a direction of an axis of the tubular portion 4, and a plurality (three in the figure) of projecting anti-slip projections 4c equally spaced apart in the vicinity of an opening at the rear end of the tubular portion 4, said projections 4c being integral with the tubular portion 4.

Charged into the inner end of the tubular portion 4 are two front and rear packings e having through-holes 41', 42', 43' and 44' in communication with said ports 41 to 44.

The receiving chamber 3 is formed into a closed-end tubular configuration having an opening 3a in its upper surface, and is formed in the center of a bottom wall thereof with a through-hole 3b.

Since the aforementioned cooling water spray port 51 is communicated with both the passages 54 and 55, the former is formed by secondary working by means of a drill or the like after the casing 5 has been formed. However, all parts except that mentioned above, that is, the ports 41 to 44, passages 52 to 55, opening 3a, through-hole 3b, key 4b, anti-slip projection 4c and the like are formed simultaneously when the casing 5 is molded. In short, the head portion b is completed if the cooling water spray port 51 is provided after the casing 5 has been molded.

The air turbine c is assembled by charging in sequence an elastic member 9, a lower bearing 6, a rotary shaft 7 and a turbine 8 and a lower bearing 6 into the receiving chamber 3 and attaching a lid member 10 to an opening 3a in the upper surface of the receiving chamber 3.

A rotary shaft 7 has a tubular shape formed of synthetic resin or metal as desired and is formed integral with a turbine 8 provided in the outer periphery thereof and having a plurality of blades. The rotary shaft 7 has an upper end loosely inserted into a hole 10a bored in a lid member 10 and a lower end loosely inserted into a through-hole 3b in a bottom wall of the receiving chamber 3, both the upper and lower ends being supported by the bearing 6 and being rotatably supported within the receiving chamber 3.

In the upper and lower bearings 6, wall portions 62 in sliding contact with upper and lower edges of the turbine 8 are provided on upper and lower inner rings slipped over the rotary shaft 7, lid portions 64 opposed to said wall portions 62 are provided on upper and lower outer rings 63 surrounding the inner rings 61, and a plurality of steel balls 65 are received between said inner rings 61 and said outer rings 63. The steel balls 65 are charged free to roll into holes 66' bored parallel with rings 66 set in the intermediary between the inner ring 61 and the outer ring 63. When this ring 66 is set between the inner ring 61 and the outer ring 63, all steel balls 65 are set. In charging the steel balls 65 into the holes 66', grease is coated on the steel balls 65 or holes 66' so that the tackiness thereof is utilized to prevent the steel balls 65 from being fallen. That grease can be utilized as it is as a lubricant for the bearing 6.

The upper and lower inner rings 61 are pressed or adherred to the rotary shaft 7 to be integral with the rotary shaft 7 whereby the turbine chamber 8' is formed between the upper and lower walls 62 and 62. The inner ring 61 having the wall 62, the outer ring 63 having the lid 64 and the ring 66 are in the form of an integral molded article by a metal press or diecast, and surface hardening treatment is applied thereto to increase a hardness.

The turbine chamber 8' is communicated with the air supply flowpassage 1a through the passage 52 and the air supply port 41 and communicated with the air discharge flowpassage 1b through the passage 53 and the air discharge port 42. The turbine 8 provided integral with the rotary shaft 7 is rotatably received into the turbine chamber 8'.

The elastic member 9 serves to press the bearings 6, 6 and turbine 8 toward the lid member 10 and is integrally formed into a ring-like configuration formed of an elastic material as desired. The lid member 10 is engaged at a shoulder provided in the opening 3a of the upper surface of the receiving chamber 3 and attached to the opening 3a. Both the bearings 6, 6 and turbine 8 arranged between the lid member 3a and the elastic member 9 are held under constant pressure by elasticity of the elastic member 9. Thereby, the bearings 6 and turbine 8 are smoothly rotated.

A stop-screw 11 is rotatably engaged at an end of the rotary shaft 7. A collet 12 is inserted into the rotary shaft 7.

The collet 12 is of a cylindrical configuration that can be rotatably inserted into the rotary shaft 7, and is an integral molded article formed of synthetic resin provided interiorly of the upper end thereof with a tapped hole 12a with which is threadedly engaged the stop-screw 11 and at the lower end thereof with a slotted mounting hole 12b. The collet 12 is threadedly moved forward and backward within the rotary shaft 7 by rotation of the screw 11 so that the mounting hole 12b is tightened to tightly hold a cutting tool d inserted into the mounting hole 12b. When under said tightened state, the stop-screw 11 is turned to slightly move forward and backward the collet 12, fine adjustment in position of the cutting tool d can be made.

In the handpiece according to the present embodiment constructed as described above, when the key 4b to be inserted into the key way a11 is used as a guide and the fore-end of the handpiece body a (the end a1' of the front case a1) is forced into the tubular portion 4 of the head portion b, the respective anti-slip projections 4c come into elastic engagement with the recesses a12 whereby the head portion b is attached to the extreme end of the handpiece body a in a one-touch manner. At that time, the springing forces of the packings e damp collision between the extreme end of the handpiece body a and the inner end of the tubular portion 4 and urges the handpiece body a and the head portion b in a direction of moving away from each other to further insure the elastic engagement between the projections 4c an the recesses a12.

Simultaneously, the air supply flowpassage 1a and the air discharge flowpassage 1b in the handpiece body a are communicated with the turbine chamber 8' of the air turbine c, and the cooling water flowpassage 1c and the air flowpassage 1d are communicated with the cooling water spray port 51. The turbine 8 is rotated at high speed by compressed air which returns to the turbine chamber 8' from the air supply flowpassage 1a and flows down through the air discharge flowpassage 1b to rotate the cutting tool d at high speed. Thereby, the affected tooth part is removed and cut, and the cooling water supplied from the cooling water flowpassage 1c is sprayed from the spray port 51 by the spraying air supplied from the air flowpassage 1d to cool the cut affected part.

Upon termination of the treatment, the handpiece body a and the head portion b are pulled in a direction of moving away from each other to release the elastic engagement between the projection 4c and the recess a12 whereby the head portion b is removed from the extreme end of the handpiece body a in a one-touch manner. The removed and used head portion b is discarded, and the handpiece body a is subjected to high temperature sterilization by boiling, after which an unused new head portion b is attached to the extreme end of the handpiece body a as mentioned above for treatment of a next patient.

According to the above-described configuration, since constituent parts for mounting the head portion b (projection 4c, recess a12, key 4b and key way a11) are covered with the casing 5 of the head portion b, there occurs no possible lowering of operability of the handpiece during treatment due to the projection of parts (for example, such as a collar fitted in the outer periphery of the tubular portion 4) for mounting the head portion b to a holding portion. Furthermore, in the case where when the extreme end of the handpiece is bended to improve the operability, there is no possibility that an operating allowance of the collar or the like cannot be secured.

Furthermore, the collet 12 or the like for supporting the head portion b, the air turbine c and the cutting tool d are configured as described above whereby only the cooling water spray port 51 need be subjected to the secondary working by means of a drill or the like but those except the aforesaid parts can be provided by the press molding or die molding which require no secondary working. Moreover, the internal construction of the head portion b comprised of these parts can be simplified to provide the head portion b at extremely low cost.

In the present embodiment, the recess a12 and the key way a11 are provided on the side of the handpiece a, and the anti-slip projection 4c and the key 4b are provided on the side of the head portion b, but the present invention is not limited thereto. It is possible that the anti-slip projection 4c is provided on the side of the handpiece body a, and the recess a12 is provided on the side of the head portion b, or the key 4b is provided on the side of the handpiece a, and the key way a11 is provided on the side of the head portion b. Similarly, it is suitably designed so that the recess a12 is comprised of a plurality of recesses matched to the projections 4c or the projections 4c are formed to be annular matched to the recesses a12. These can be suitably selected according to convenience in molding the handpiece body a or head portion b.

The handpiece for dental medical treatment according to the present invention is constructed as described above and exhibits the following effects.

Since the head portion encasing therein the air turbine is detachably mounted on the handpiece body, the air turbine portion having no durability with respect to the high temperature sterilization by boiling is discarded every treatment whereas only the handpiece body capable of withstanding the high temperature sterilization is repeatedly used. Thereby, the aseptic state of the handpiece body can be maintained to positively prevent possible secondary infection such as AIDS, hepatitis, etc. resulting from the dental treatment. In addition, the sterilization method is carried out by boiling which is most effective and inexpensive for prevention of infection to prevent a steep rise of medical expense and a considerable increase of burden by a patient.

Further, since the head portion is detachably mounted by the elastic engaging means comprising anti-slip projections and recesses, the head portion can be detachably mounted on the handpiece body in a one-touch manner. Moreover, the constituent parts (the aforesaid elastic engaging means) for detachably mounting the head portion are covered with the casing, and therefore, there is no possibility that the operability of the handpiece is lowered during treatment due to the projection of parts for mounting the head portion, for example, such as a collar fitted in the outer periphery of the head portion to the holding portion during treatment. Furthermore, in the case where the extreme end of the handpiece is bent to improve the aforementioned operability, there is no possibility that the operating allowance of parts such as the collar cannot be secured.

Furthermore, by the provision of configurations as in claims 2 to 4, the internal construction of the head portion encasing therein the air turbine is simplified, and most of constituent members can be provided by molding which requires no secondary working to render possible the provision of the whole head portion at extremely low cost. Since the head portion can be discarded, an increase in cost of the whole handpiece can be prevented to effectively prevent the secondary infection of the AIDS, hepatitis, etc.

What is claimed is:

1. A handpiece for dental medical treatment in which an air turbine rotated at high speed by compressed air is encased in and a cooling water spray port is provided in a head portion at the extreme end of a handpiece body interiorly provided with a compressed air supply flowpassage and discharge flowpassage, a cooling water flow-passage and discharge flowpassage, a cooling water flowpassage and a cooling water spraying air flowpassage, and a cutting tool is inserted into a tubular rotary shaft of said air turbine, characterized in that a head portion is formed separately from a handpiece body, a tubular portion slopped over an extreme end of the handpiece body is provided at a rear end thereof, air supply and discharge ports through which air supply and discharge flowpassages and a turbine chamber for an air turbine are communicated and a cooling water port and a spray air port through which a cooling water flowpassage and an air flowpassage are communicated with a spray port are bored at an inner end of said tubular portion, and an anti-slip projection is provided on one of an inner periphery of the tubular portion of said head portion and an outer periphery at the extreme end of the handpiece while a recess with which said projection is disengageably and elastically engaged is provided on the other; and wherein said head portion is formed with a closed-end tubular receiving chamber an upper surface of which is opened, upper and lower bearings, a rotary shaft upper and lower ends of which are supported by said bearings, a turbine provided integral with the outer periphery of said rotary shaft, and an elastic member for urging said bearings and said turbine toward the upper surface of the receiving chamber are charged into said receiving chamber, and a lid member is fitted to an opening of the upper surface of the receiving chamber to form an air turbine; and wherein a tapped hole is provided internally of an upper end of a collet inserted into the rotary shaft, and a stop screw engaged with said tapped hole is engaged at the end of the rotary shaft so that said collet is threadedly moved forward and backward by turning said stop screw to tightly hold a cutting tool inserted into a slotted mounting hole of the lower end of the collet.

2. A handpiece for dental medical treatment according to claim 1, wherein walls in sliding contact with upper and lower edges of the turbine are provided on upper and lower inner rings slipped over the rotary shaft to form a turbine chamber between both the walls, lid portions opposed to said walls are provided on upper and lower outer rings surrounding the respective inner rings, and a plurality of steel balls are received between said inner rings and said outer rings to form upper and lower bearings.

3. A handpiece for dental medical treatment comprising:

a removable head portion which is adapted to be discarded after a one-time use, in which a high speed air turbine is encased, said head portion further comprising a cooling water spray port at one end and being interiorly provided with a compressed air supply flowpassage and discharge flowpassage, a cooling water flowpassage and discharge flowpassge, a cooling water flowpassage and a cooling water spraying air flowpassage, a closed-end tubular receiving chamber, an upper surface of which is opened;

upper and lower bearings;

a rotary shaft having upper and lower ends which are supported by said upper and lower bearings;

a turbine provided integrally with the outer periphery of said rotary shaft;

an elastic member for urging said bearings and said turbine toward the upper surface of the receiving chamber after being changed into said receiving chamber;

a lid member fitted to an opening of the upper surface of said receiving chamber;

walls, provided in sliding contact with upper and lower edges of said turbine, on upper and lower inner rings slipped over said rotary shaft to form a turbine chamber between both said walls;

lid portions opposed to said walls and provided on upper and lower outer rings surrounding sad respective inner rings;

and a plurality of steel balls received between said inner rings and said outer rings to form upper and lower bearings, wherein a tapped hole is provided internally of an upper end of a collet inserted into said rotary shaft, and a stop screw engaged with said tapped hole, is engaged at the end of said rotary shaft so that said collet is threadedly moved forward and backward by turning said stop screw to tightly hold a cutting tool, inserted into a slotted mounting hole at the lower end of said collet;

said handpiece further comprising a reusable handpiece body which is adapted to be held in the hand of a user, said handpiece body further comprising, at one end thereof, means for locking with said head, and at another end of said body, means for engaging a supply hose for supplying at least air and water.

* * * * *